(12) United States Patent
Cao et al.

(10) Patent No.: US 10,838,086 B2
(45) Date of Patent: Nov. 17, 2020

(54) RADIATION DETECTOR WITH DYNAMICALLY ALLOCATED MEMORY FOR PARTICLE COUNTING

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

(*) Notice: Subject to any disclaimer, the term of this patent is extended or adjusted under 35 U.S.C. 154(b) by 0 days.

(21) Appl. No.: 16/185,393

(22) Filed: Nov. 9, 2018

(65) Prior Publication Data
US 2019/0094396 A1 Mar. 28, 2019

Related U.S. Application Data

(63) Continuation of application No. PCT/CN2017/072152, filed on Jan. 23, 2017.

(51) Int. Cl.
| | |
|---|---|
| *G01T 1/29* | (2006.01) |
| *G01T 1/24* | (2006.01) |
| *G01T 1/208* | (2006.01) |
| *H04N 5/32* | (2006.01) |
| *H04N 5/378* | (2011.01) |
| *A61B 6/00* | (2006.01) |
| *G01N 23/04* | (2018.01) |

(Continued)

(52) U.S. Cl.
CPC .......... *G01T 1/2928* (2013.01); *A61B 6/4208* (2013.01); *G01N 23/04* (2013.01); *G01N 23/203* (2013.01); *G01T 1/208* (2013.01); *G01T 1/24* (2013.01); *G01T 1/243* (2013.01); *G01T 1/245* (2013.01); *G01T 1/247* (2013.01); *G06F 3/0608* (2013.01); *G06F 3/0671* (2013.01); *H04N 5/32* (2013.01); *H04N 5/378* (2013.01); *H04N 5/77* (2013.01)

(58) Field of Classification Search
CPC ....... G01T 1/2928; G01T 1/208; G01T 1/245; G01T 1/24; G01T 1/247; G01T 1/243; H04N 5/378; H04N 5/32; G01N 23/203; G01N 23/04; A61B 6/4208
See application file for complete search history.

(56) References Cited

U.S. PATENT DOCUMENTS

| | | | |
|---|---|---|---|
| 4,694,398 A | 9/1987 | Croteau | |
| 5,559,956 A * | 9/1996 | Sukegawa | G06F 12/0246 |
| | | | 711/E12.014 |

(Continued)

FOREIGN PATENT DOCUMENTS

| | | |
|---|---|---|
| CN | 103975580 A | 8/2014 |
| TW | 201640142 A | 11/2016 |

(Continued)

*Primary Examiner* — Michael C Bryant
(74) *Attorney, Agent, or Firm* — IPro, PLLC

(57) ABSTRACT

Disclosed herein is a radiation detector, comprising: a radiation absorption layer configured to absorb a radiation; a plurality of counters each associated with a bin and configured to register a number of particles of the radiation particles absorbed by the detector; a memory comprising a plurality of units, which can be dynamically allocated to the counters.

35 Claims, 21 Drawing Sheets

(51) Int. Cl.
*G01N 23/203* (2006.01)
*G06F 3/06* (2006.01)
*H04N 5/77* (2006.01)

(56) References Cited

U.S. PATENT DOCUMENTS

| | | | |
|---|---|---|---|
| 6,408,050 B1 * | 6/2002 | Han | G01T 1/17 |
| | | | 378/98.11 |
| 2002/0117627 A1 * | 8/2002 | Jimbo | G01T 1/161 |
| | | | 250/370.13 |
| 2005/0139757 A1 * | 6/2005 | Iwanczyk | G01T 1/2928 |
| | | | 250/239 |
| 2009/0290680 A1 * | 11/2009 | Tumer | G01T 1/247 |
| | | | 378/62 |
| 2010/0020924 A1 * | 1/2010 | Steadman Booker | G01T 1/17 |
| | | | 378/19 |
| 2010/0232633 A1 * | 9/2010 | Nielsen | H04R 25/305 |
| | | | 381/317 |
| 2013/0028382 A1 | 1/2013 | Spahn | |
| 2013/0284940 A1 * | 10/2013 | Herrmann | G01T 1/17 |
| | | | 250/393 |
| 2014/0185752 A1 | 7/2014 | Lu et al. | |
| 2014/0334600 A1 * | 11/2014 | Lee | G01N 23/04 |
| | | | 378/62 |
| 2016/0124667 A1 | 5/2016 | Lee et al. | |
| 2018/0081071 A1 * | 3/2018 | Cao | H01L 27/14661 |

FOREIGN PATENT DOCUMENTS

| | | |
|---|---|---|
| TW | 201643418 A | 12/2016 |
| WO | 2016197338 A1 | 12/2016 |

\* cited by examiner

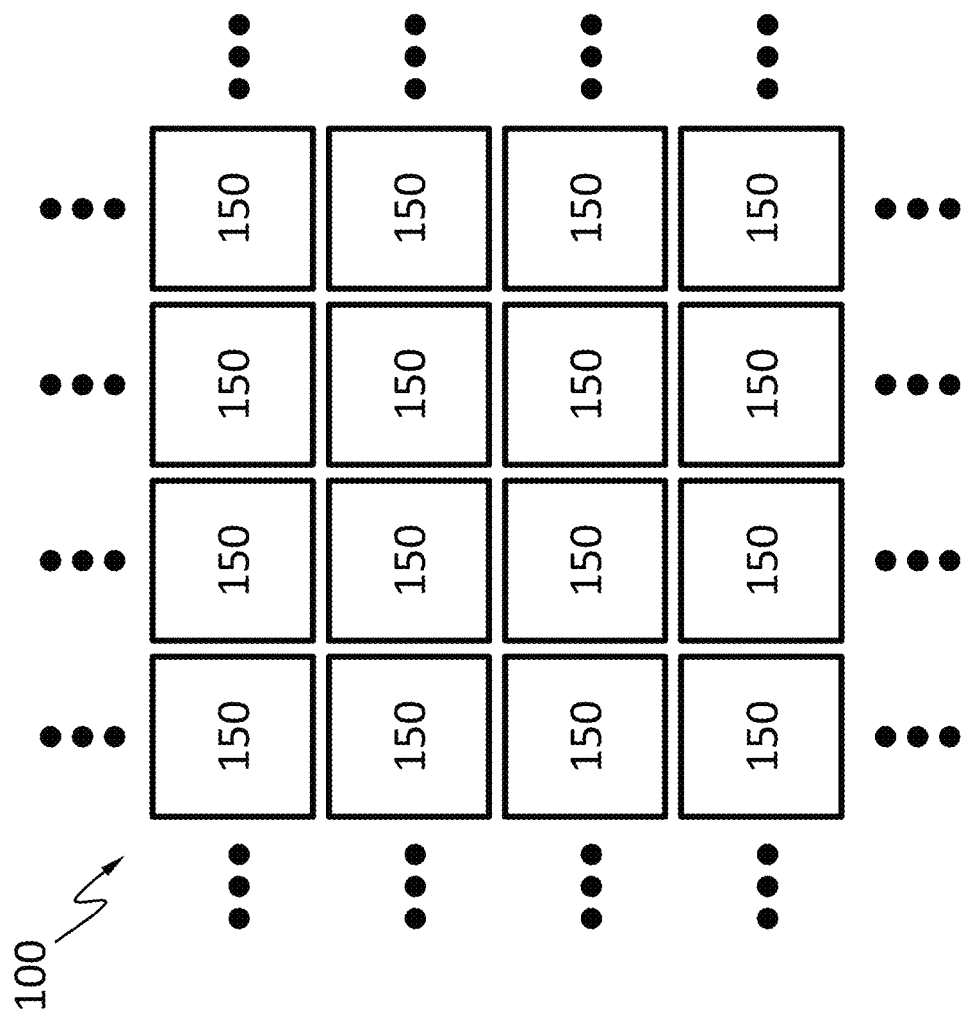

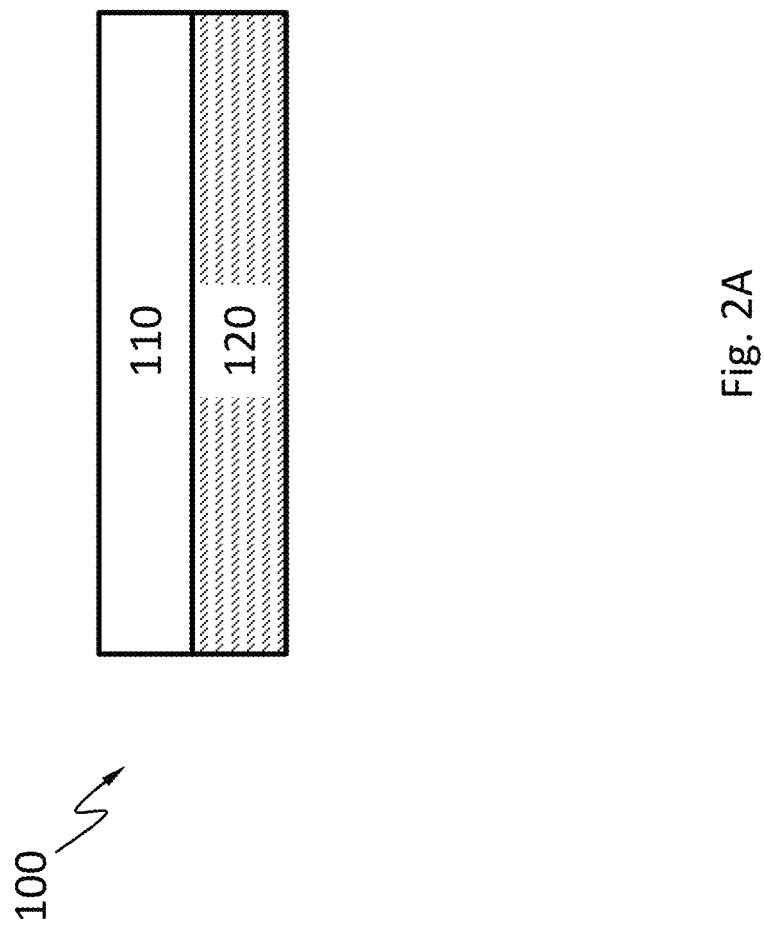

RADIATION DETECTOR WITH DYNAMICALLY ALLOCATED MEMORY FOR PARTICLE COUNTING

TECHNICAL FIELD

The disclosure herein relates to methods and apparatuses configured to dynamically allocate memory for particle counting in a radiation detector such as an X-ray detector.

BACKGROUND

A radiation detector is a device that measures a property of a radiation. Examples of the property may include a spatial distribution of the intensity, phase, and polarization of the radiation. The radiation may be one that has interacted with a subject. For example, the radiation measured by the radiation detector may be a radiation that has penetrated or reflected from the subject. The radiation may be an electromagnetic radiation such as infrared light, visible light, ultraviolet light, X-ray or y-ray.

One type of radiation detectors is based on interaction between the radiation and a semiconductor. For example, a radiation detector of this type may comprise a semiconductor layer that absorbs the radiation and then generates charge carriers (e.g., electrons and holes) whose amount is proportional to the energy of the radiation. The charge carriers are collected and counted by a circuitry to determine the energy of the radiation and the process repeats for the next incident radiation. A spectrum may be compiled by counting the number of detected radiation as a function of its energy. The speed of these detectors is limited because the charge carriers generated by radiation must be collected before the detector is ready for next detection.

SUMMARY

Disclosed herein is a radiation detector, comprising: a radiation absorption layer configured to absorb a radiation; a plurality of counters each associated with a bin and configured to register a number of particles of the radiation absorbed by the radiation absorption layer, wherein energy of the particles falls in the bin; a memory comprising a plurality of units; a processor configured to allocate the units to the counters.

According to an embodiment, the processor is configured to allocate the units to the counters based on at least one number of particles registered in the counters.

According to an embodiment, the processor is configured to allocate the units to the counters based on a rate of change of at least one number of particles registered in the counters.

According to an embodiment, the processor is configured to deallocate units.

According to an embodiment, the processor is configured to deallocate the units to the counters based on at least one number of particles registered in the counters.

According to an embodiment, the processor is configured to deallocate the units to the counters based on a rate of change of at least one number of particles registered in the counters.

According to an embodiment, the radiation is X-ray.

According to an embodiment, the radiation detector further comprises a controller, wherein the controller is configured to determine whether an energy of a particle of the radiation falls into the bin; and wherein the controller is configured to cause the number registered by the counter associated with the bin to increase by one.

According to an embodiment, the radiation detector further comprises: a first voltage comparator configured to compare a voltage of an electric contact of the radiation absorption layer to a first threshold; a second voltage comparator configured to compare the voltage to a second threshold; a controller is configured to start a time delay from a time at which the first voltage comparator determines that an absolute value of the voltage equals or exceeds an absolute value of the first threshold.

According to an embodiment, the controller is configured to activate the second voltage comparator at a beginning or expiration of the time delay.

According to an embodiment, the radiation detector further comprises a voltmeter, wherein the controller is configured to cause the voltmeter to measure the voltage upon expiration of the time delay.

According to an embodiment, the controller is configured to determine a particle energy based on a value of the voltage measured upon expiration of the time delay.

According to an embodiment, the detector comprises a capacitor module electrically connected to the electric contact, wherein the capacitor module is configured to collect charge carriers from the electric contact.

According to an embodiment, the controller is configured to connect the electrode to an electrical ground.

According to an embodiment, a rate of change of the voltage is substantially zero at expiration of the time delay.

According to an embodiment, a rate of change of the voltage is substantially non-zero at expiration of the time delay.

According to an embodiment, the radiation absorption layer comprises a diode.

According to an embodiment, the radiation absorption layer comprises silicon, germanium, GaAs, CdTe, CdZnTe, or a combination thereof.

According to an embodiment, the radiation detector does not comprise a scintillator.

According to an embodiment, the radiation detector comprises an array of pixels.

Disclosed herein is a system comprising any of the above radiation detectors and an X-ray source, wherein the system is configured to perform X-ray radiography on human chest or abdomen.

Disclosed herein is a system comprising any of the above radiation detectors and an X-ray source, wherein the system is configured to perform X-ray radiography on human mouth.

Disclosed herein is a cargo scanning or non-intrusive inspection (NII) system, comprising any of the above radiation detectors and an X-ray source, wherein the cargo scanning or non-intrusive inspection (NII) system is configured to form an image using backscattered X-ray.

Disclosed herein is a cargo scanning or non-intrusive inspection (NII) system, comprising the radiation detector of any of the above radiation detectors and an X-ray source, wherein the cargo scanning or non-intrusive inspection (NII) system is configured to form an image using X-ray transmitted through an object inspected.

Disclosed herein is a full-body scanner system comprising the radiation detector of any of the above radiation detectors and a radiation source.

Disclosed herein is a computed tomography (CT) system comprising the radiation detector of any of the above radiation detectors and a radiation source.

Disclosed herein is an electron microscope comprising the radiation detector of any of the above radiation detectors, an electron source and an electronic optical system.

Disclosed herein is a system comprising the radiation detector of any of the above radiation detectors, wherein the system is an X-ray telescope, or an X-ray microscopy, or wherein the system is configured to perform mammography, industrial defect detection, microradiography, casting inspection, weld inspection, or digital subtraction angiography.

Disclosed herein is a method comprising: determining whether an energy of a particle of a radiation falls into a bin; upon determination that the energy falls into the bin, causing a first number registered by a first counter associated with the bin to increase by one; determining whether the first number or a rate of change thereof satisfies a first condition; upon determination that the first number or the rate of change thereof satisfies the first condition, allocating a unit of a memory to the first counter.

According to an embodiment, the method further comprises: determining whether a second number registered by a second counter or a rate of change thereof satisfies a second condition; upon determination that the second number or the rate of change thereof satisfies the second condition, deallocating a unit of a memory from the second counter.

Disclosed herein is a method comprising: monitoring a number registered by a counter configured to count only particles of a radiation, energy of each of the particles being within a bin; determining whether the number or a rate of change thereof satisfies a first condition; upon determination that the number or the rate of change thereof satisfies the first condition, allocating a unit of a memory to the counter.

According to an embodiment, the method further comprises: determining whether the number or the rate of change thereof satisfies a second condition; upon determination that the number or the rate of change thereof satisfies the second condition, deallocating a unit of the memory from the counter.

BRIEF DESCRIPTION OF FIGURES

FIG. 1A and FIG. 1B schematically shows a radiation detector and its block diagram, according to an embodiment.

FIG. 2A schematically shows a cross-sectional view of the radiation detector.

DETAILED DESCRIPTION

FIG. 1A schematically shows a radiation detector 100, according to an embodiment. The detector has an array of pixels 150. The array may be a rectangular array, a honeycomb array, a hexagonal array or any other suitable array. Each pixel 150 is configured to detect a particle of radiation from a radiation source incident thereon and measure a characteristic (e.g., the energy of the particles, the wavelength, and the frequency) of the radiation. For example, each pixel 150 is configured to count numbers of particle of radiation incident thereon whose energy falls in a plurality of bins, within a period of time. All the pixels 150 may be configured to count the numbers of particle of radiation incident thereon within a plurality of bins of energy within the same period of time. Each pixel 150 may have its own analog-to-digital converter (ADC) configured to digitize an analog signal representing the energy of an incident particle of radiation into a digital signal. The pixels 150 may be configured to operate in parallel. For example, when one pixel 150 measures an incident particle of radiation, another pixel 150 may be waiting for a particle of radiation to arrive. The pixels 150 may not have to be individually addressable.

The detector 100 may have at least 100, 2500, 10000, or more pixels 150. The detector 100 may be configured to add the numbers of detected radiation for the bins of the same energy range counted by all the pixels 150. For example, the detector 100 may add the numbers the pixels 150 stored in a bin for energy from 70 KeV to 71 KeV, add the numbers the pixels 150 stored in a bin for energy from 71 KeV to 72 KeV, and so on. The detector 100 may compile the added numbers for the bins as a spectrum of the radiation incident on the detector 100.

Figure 1B:
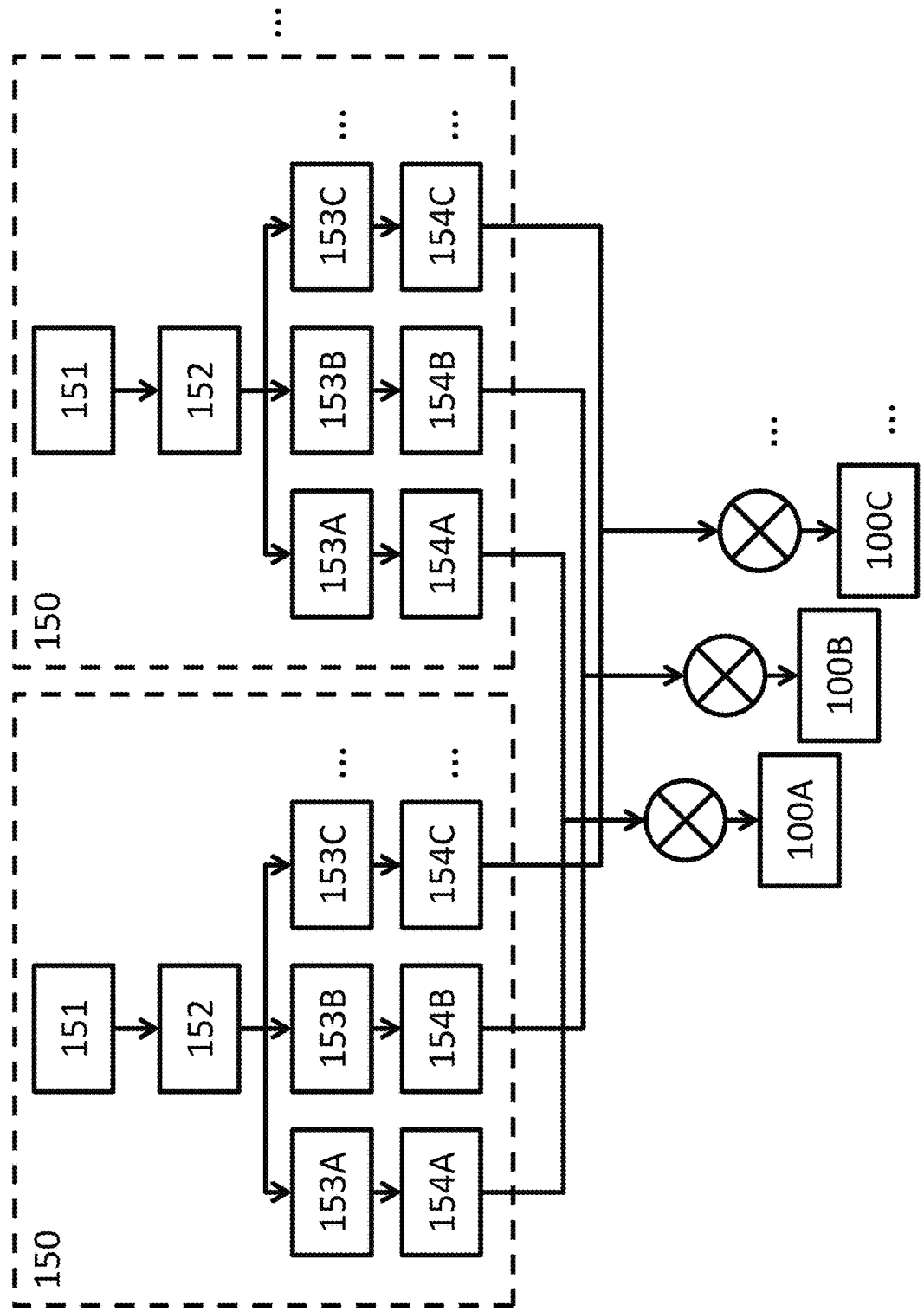

FIG. 1B schematically shows a block diagram for the detector 100, according to an embodiment. Each pixel 150 may measure the energy 151 of the radiation incident thereon. The energy 151 of the radiation is digitized (e.g., by an ADC) in step 152 into one of a plurality of bins 153A, 153B, 153C . . . . The bins 153A, 153B, 153C . . . each have a corresponding counter 154A, 154B and 154C, respectively. When the energy 151 is allocated into a bin, the number stored in the corresponding counter increases by one. The detector 100 may added the numbers stored in all the counters corresponding to bins for the same energy range in the pixels 150. For example, the numbers stored in all the counters 154C in all pixels 150 may be added and stored in a global counter 100C for the same energy range. The numbers stored in all the global counters may be compiled into an energy spectrum of the radiation incident on the detector 100.

FIG. 2A schematically shows a cross-sectional view of the radiation detector 100, according to an embodiment. The radiation detector 100 may include a radiation absorption layer 110 and an electronics layer 120 (e.g., an ASIC) for processing or analyzing electrical signals incident radiation generates in the radiation absorption layer 110. The detector 100 may or may not include a scintillator. The radiation absorption layer 110 may include a semiconductor material such as, silicon, germanium, GaAs, CdTe, CdZnTe, or a combination thereof. The semiconductor may have a high mass attenuation coefficient for the radiation of interest.

Figure 2B:
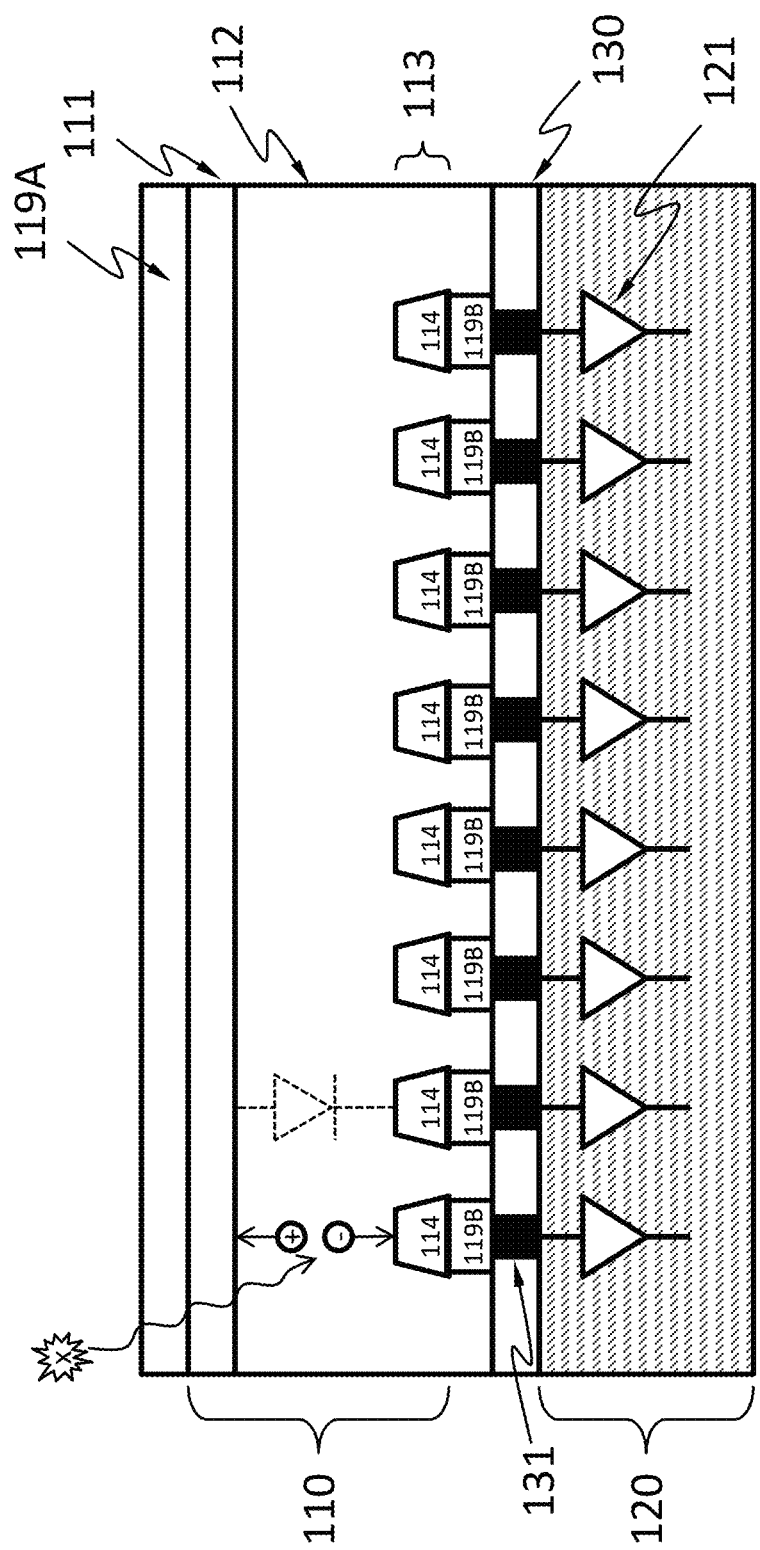
FIG. 2B schematically shows a detailed cross-sectional view of the radiation detector.

As shown in a detailed cross-sectional view of the radiation detector 100 in FIG. 2B, according to an embodiment, the radiation absorption layer 110 may include one or more diodes (e.g., p-i-n or p-n) formed by a first doped region 111, one or more discrete regions 114 of a second doped region 113. The second doped region 113 may be separated from the first doped region 111 by an optional the intrinsic region 112. The discrete portions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 2B, each of the discrete regions 114 of the second doped region 113 forms a diode with the first doped region 111 and the optional intrinsic region 112. Namely, in the example in FIG. 2B, the radiation absorption layer 110 has a plurality of diodes having the first doped region 111 as a shared electrode. The first doped region 111 may also have discrete portions.

When radiation from the radiation source hits the radiation absorption layer 110 including diodes, the radiation photon may be absorbed and generate one or more charge carriers by a number of mechanisms. The charge carriers may drift to the electrodes of one of the diodes under an electric field. The field may be an external electric field. The electric contact 119B may include discrete portions each of which is in electric contact with the discrete regions 114. In an embodiment, the charge carriers may drift in directions such that the charge carriers generated by a single particle of the radiation are not substantially shared by two different discrete regions 114 ("not substantially shared" here means less than 2%, less than 0.5%, less than 0.1%, or less than 0.01% of these charge carriers flow to a different one of the discrete regions 114 than the rest of the charge carriers). Charge carriers generated by a particle of the radiation incident around the footprint of one of these discrete regions 114 are not substantially shared with another of these discrete regions 114. A pixel 150 associated with a discrete region 114 may be an area around the discrete region 114 in which substantially all (more than 98%, more than 99.5%, more than 99.9%, or more than 99.99% of) charge carriers generated by a particle of the radiation incident therein flow to the discrete region 114. Namely, less than 2%, less than 1%, less than 0.1%, or less than 0.01% of these charge carriers flow beyond the pixel.

Figure 2C:
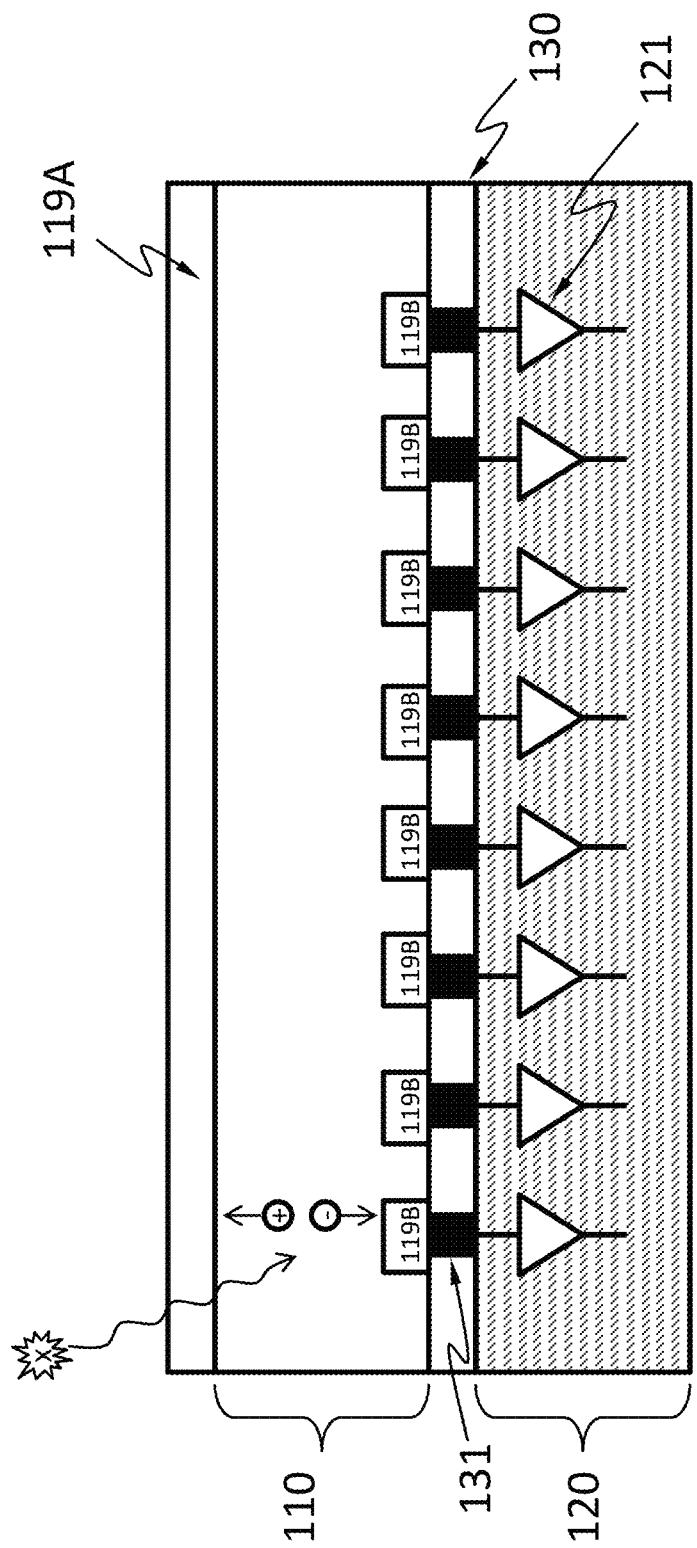
FIG. 2C schematically shows an alternative detailed cross-sectional view of the radiation detector.

As shown in an alternative detailed cross-sectional view of the detector 100 in FIG. 2C, according to an embodiment, the radiation absorption layer 110 may include a resistor of a semiconductor material such as, silicon, germanium, GaAs, CdTe, CdZnTe, or a combination thereof, but does not include a diode. The semiconductor may have a high mass attenuation coefficient for the radiation of interest.

When the radiation hits the radiation absorption layer 110 including a resistor but not diodes, it may be absorbed and generate one or more charge carriers by a number of mechanisms. A particle of the radiation may generate 10 to 100000 charge carriers. The charge carriers may drift to the electric contacts 119A and 119B under an electric field. The field may be an external electric field. The electric contact 119B includes discrete portions. In an embodiment, the charge carriers may drift in directions such that the charge carriers generated by a single particle of the radiation are not substantially shared by two different discrete portions of the electric contact 119B ("not substantially shared" here means less than 2%, less than 0.5%, less than 0.1%, or less than 0.01% of these charge carriers flow to a different one of the discrete portions than the rest of the charge carriers). Charge carriers generated by a particle of the radiation incident around the footprint of one of these discrete portions of the electric contact 119B are not substantially shared with another of these discrete portions of the electric contact 119B. A pixel 150 associated with a discrete portion of the electric contact 119B may be an area around the discrete portion in which substantially all (more than 98%, more than 99.5%, more than 99.9% or more than 99.99% of) charge carriers generated by a particle of the radiation incident therein flow to the discrete portion of the electric contact 119B. Namely, less than 2%, less than 0.5%, less than 0.1%, or less than 0.01% of these charge carriers flow beyond the pixel associated with the one discrete portion of the electric contact 119B.

The electronics layer 120 may include an electronic system 121 suitable for processing or interpreting signals generated by the radiation incident on the radiation absorption layer 110. The electronic system 121 may include an analog circuitry such as a filter network, amplifiers, integrators, and comparators, or a digital circuitry such as a microprocessors, and memory. The electronic system 121 may include one or more ADCs. The electronic system 121 may include components shared by the pixels or components dedicated to a single pixel. For example, the electronic system 121 may include an amplifier dedicated to each pixel and a microprocessor shared among all the pixels. The electronic system 121 may be electrically connected to the pixels by vias 131. Space among the vias may be filled with a filler material 130, which may increase the mechanical stability of the connection of the electronics layer 120 to the radiation absorption layer 110. Other bonding techniques are possible to connect the electronic system 121 to the pixels without using vias.

Figure 3A:
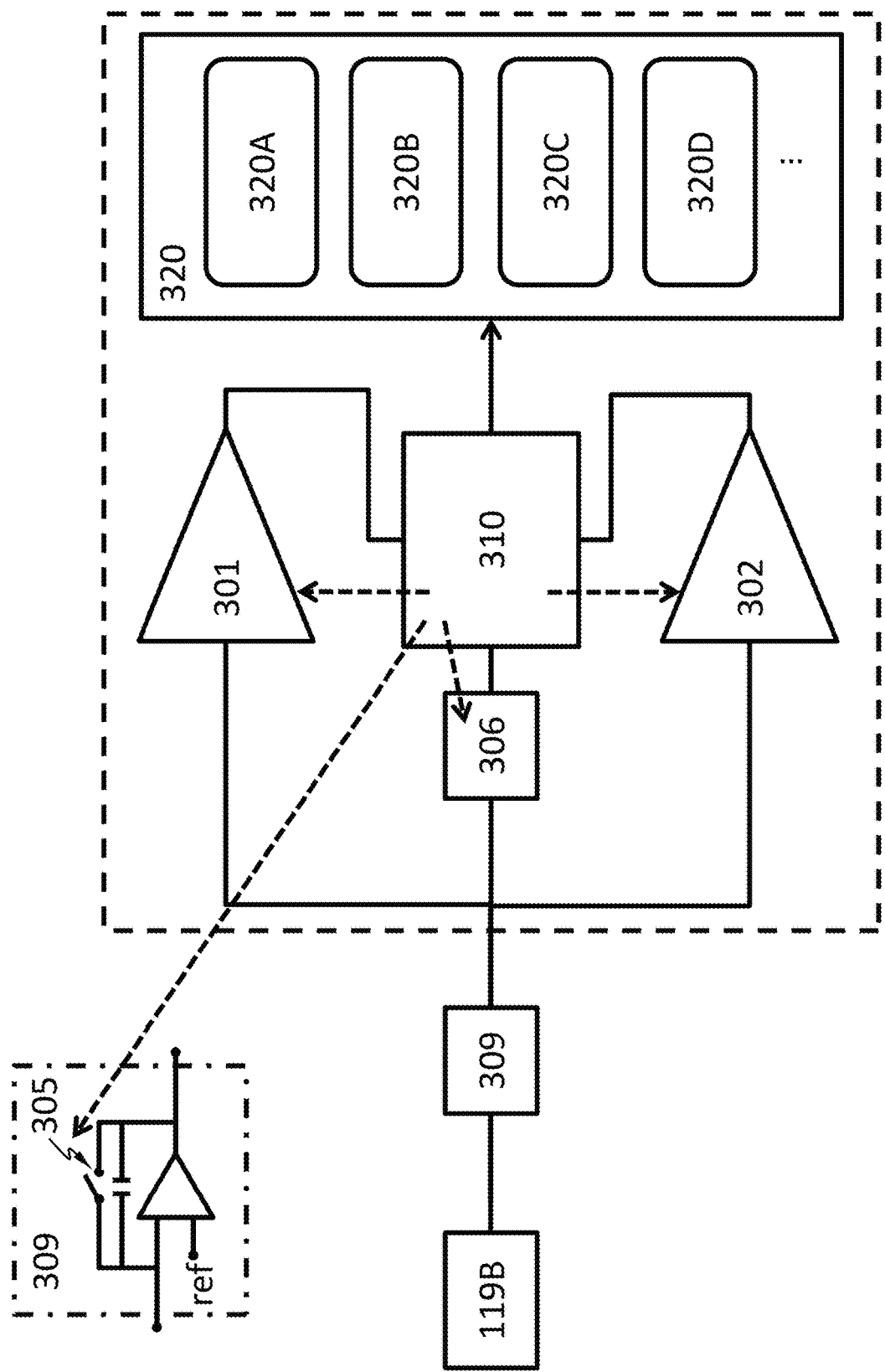
FIG. 3A and FIG. 3B each show a component diagram of the electronic system of the detector, according to an embodiment.
Figure 3B:
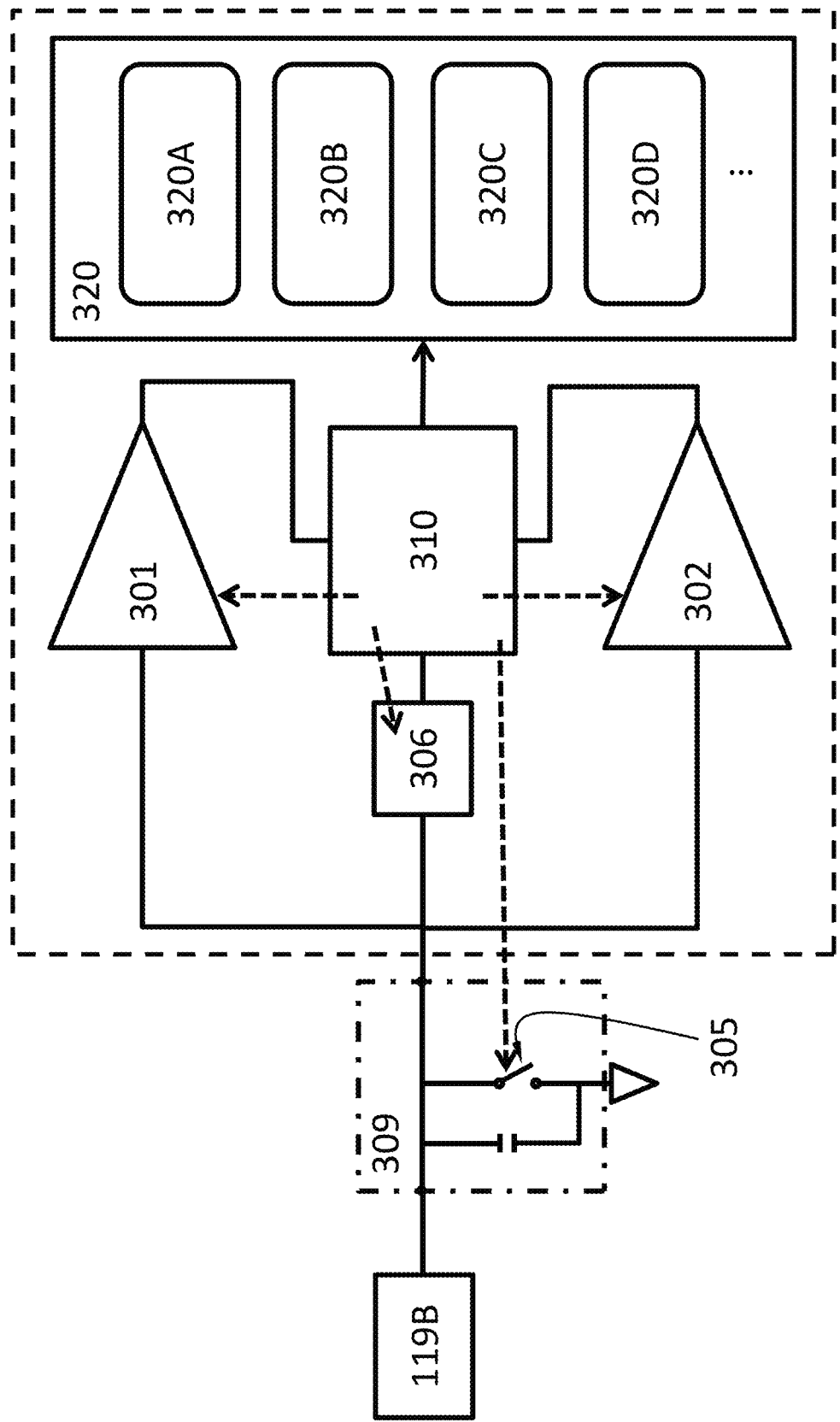

FIG. 3A and FIG. 3B each show a component diagram of the electronic system 121, according to an embodiment. The electronic system 121 may include a first voltage comparator 301, a second voltage comparator 302, a plurality of counters 320 (including counters 320A, 320B, 320C, 320D . . . ), a switch 305, an ADC 306 and a controller 310.

The first voltage comparator 301 is configured to compare the voltage of a discrete portion of the electric contact 119B to a first threshold. The first voltage comparator 301 may be configured to monitor the voltage directly, or calculate the voltage by integrating an electric current flowing through the diode or electrical contact over a period of time. The first voltage comparator 301 may be controllably activated or deactivated by the controller 310. The first voltage comparator 301 may be a continuous comparator. Namely, the first voltage comparator 301 may be configured to be activated continuously, and monitor the voltage continuously. The first voltage comparator 301 configured as a continuous comparator reduces the chance that the system 121 misses signals generated by an incident particle of radiation. The first voltage comparator 301 configured as a continuous comparator is especially suitable when the incident particle of radiation intensity is relatively high. The first voltage comparator 301 may be a clocked comparator, which has the benefit of lower power consumption. The first voltage comparator 301 configured as a clocked comparator may cause the system 121 to miss signals generated by some incident particles of radiation. When the incident radiation intensity is low, the chance of missing an incident radiation particle is low because the time interval between two successive particles is relatively long. Therefore, the first voltage comparator 301 configured as a clocked comparator is especially suitable when the incident radiation intensity is relatively low. The first threshold may be 1-5%, 5-10%, 10%-20%, 20-30%, 30-40% or 40-50% of the maximum voltage one incident particle of radiation may generate on the electric contact 119B. The maximum voltage may depend on the energy of the incident particle of radiation (i.e., the wavelength of the incident radiation), the material of the radiation absorption layer 110, and other factors. For example, the first threshold may be 50 mV, 100 mV, 150 mV, or 200 mV.

The second voltage comparator 302 is configured to compare the voltage to a second threshold. The second voltage comparator 302 may be configured to monitor the voltage directly, or calculate the voltage by integrating an electric current flowing through the diode or the electrical contact over a period of time. The second voltage comparator 302 may be a continuous comparator. The second voltage comparator 302 may be controllably activate or deactivated by the controller 310. When the second voltage comparator 302 is deactivated, the power consumption of the second voltage comparator 302 may be less than 1%, less than 5%, less than 10% or less than 20% of the power consumption when the second voltage comparator 302 is activated. The absolute value of the second threshold is greater than the absolute value of the first threshold. As used herein, the term "absolute value" or "modulus" |x| of a real number x is the non-negative value of x without regard to its sign. Namely, $$|x| = \begin{cases} x, & \text{if } x \geq 0 \\ -x, & \text{if } x \leq 0 \end{cases}.$$

The second threshold may be 200%-300% of the first threshold. For example, the second threshold may be 100 mV, 150 mV, 200 mV, 250 mV or 300 mV. The second voltage comparator 302 and the first voltage comparator 301 may be the same component. Namely, the system 121 may have one voltage comparator that can compare a voltage with two different thresholds at different times.

The first voltage comparator 301 or the second voltage comparator 302 may include one or more op-amps or any other suitable circuitry. The first voltage comparator 301 or the second voltage comparator 302 may have a high speed to allow the system 121 to operate under a high flux of incident radiation. However, having a high speed is often at the cost of power consumption.

The controller 310 may be a hardware component such as a microcontroller and a microprocessor. The controller 310 is configured to start a time delay from a time at which the first voltage comparator 301 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electrical contact is used. The controller 310 may be configured to keep deactivated the second voltage comparator 302, the counter 320 and any other circuits the operation of the first voltage comparator 301 does not require, before the time at which the first voltage comparator 301 determines that the absolute value of the voltage equals or exceeds the absolute value of the first threshold. The time delay may expire after the voltage becomes stable, i.e., the rate of change of the voltage is substantially zero. The phase "the rate of change is substantially zero" means that temporal change is less than 0.1%/ns. The phase "the rate of change is substantially non-zero" means that temporal change of the voltage is at least 0.1%/ns.

The controller 310 may be configured to activate the second voltage comparator during (including the beginning and the expiration) the time delay. In an embodiment, the controller 310 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 310 itself may be deactivated until the output of the first voltage comparator 301 activates the controller 310 when the absolute value of the voltage equals or exceeds the absolute value of the first threshold.

The controller 310 may be configured to cause the number registered by one of the counters 320 to increase by one, if, during the time delay, the second voltage comparator 302 determines that the absolute value of the voltage equals or exceeds the absolute value of the second threshold, and the energy of the particle of radiation falls in the bin associated with the counter 320.

The controller 310 may be configured to cause the ADC 306 to digitize the voltage upon expiration of the time delay and determine based on the voltage which bin the energy of the particle of radiation falls in.

The controller 310 may be configured to connect the electric contact 119B to an electrical ground, so as to reset the voltage and discharge any charge carriers accumulated on the electric contact 119B. In an embodiment, the electric contact 119B is connected to an electrical ground after the expiration of the time delay. In an embodiment, the electric contact 119B is connected to an electrical ground for a finite reset time period. The controller 310 may connect the electric contact 119B to the electrical ground by controlling the switch 305. The switch may be a transistor such as a field-effect transistor (FET).

The ADC 306 may feed the voltage it measures to the controller 310 as an analog or digital signal. The ADC may be a successive-approximation-register (SAR) ADC (also called successive approximation ADC). An SAR ADC digitizes an analog signal via a binary search through all possible quantization levels before finally converging upon a digital output for the analog signal. An SAR ADC may have four main subcircuits: a sample and hold circuit to acquire the input voltage ($V_{in}$), an internal digital-analog converter (DAC) configured to supply an analog voltage comparator with an analog voltage equal to the digital code output of the successive approximation register (SAR), the analog voltage comparator that compares $V_{in}$ to the output of the internal DAC and outputs the result of the comparison to the SAR, the SAR configured to supply an approximate digital code of $V_{in}$ to the internal DAC. The SAR may be initialized so that the most significant bit (MSB) is equal to a digital 1. This code is fed into the internal DAC, which then supplies the analog equivalent of this digital code ($V_{ref}/2$) into the comparator for comparison with $V_{in}$. If this analog voltage exceeds $V_{in}$ the comparator causes the SAR to reset this bit; otherwise, the bit is left a 1. Then the next bit of the SAR is set to 1 and the same test is done, continuing this binary search until every bit in the SAR has been tested. The resulting code is the digital approximation of $V_{in}$ and is finally output by the SAR at the end of the digitization.

The system 121 may include a capacitor module 309 electrically connected to the electric contact 119B, wherein the capacitor module is configured to collect charge carriers from the electric contact 119B. The capacitor module can include a capacitor in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path. Charge carriers from the electrode accumulate on the capacitor over a period of time ("integration period") (e.g., as shown in FIG. 6, between $t_s$ to $t_0$). After the integration period has expired, the capacitor voltage is sampled by the ADC 306 and then reset by a reset switch. The capacitor module 309 can include a capacitor directly connected to the electric contact 119B.

The counter 320 of each pixel is associated with a plurality of bins for an energy range. For example, counter 320A may be associated with a bin for particles with energy of 70-71 KeV, counter 320B may be associated with a bin for 71-72 KeV, counter 320C may be associated with a bin for 72-73 KeV, counter 320D may be associated with a bin for 73-74 KeV. When the energy of an incident particle of radiation is determined by the ADC 306 to be in the bin the counter 320 is associated with, the number registered in the bin of counter 320 is increased by one.

Figure 4A:
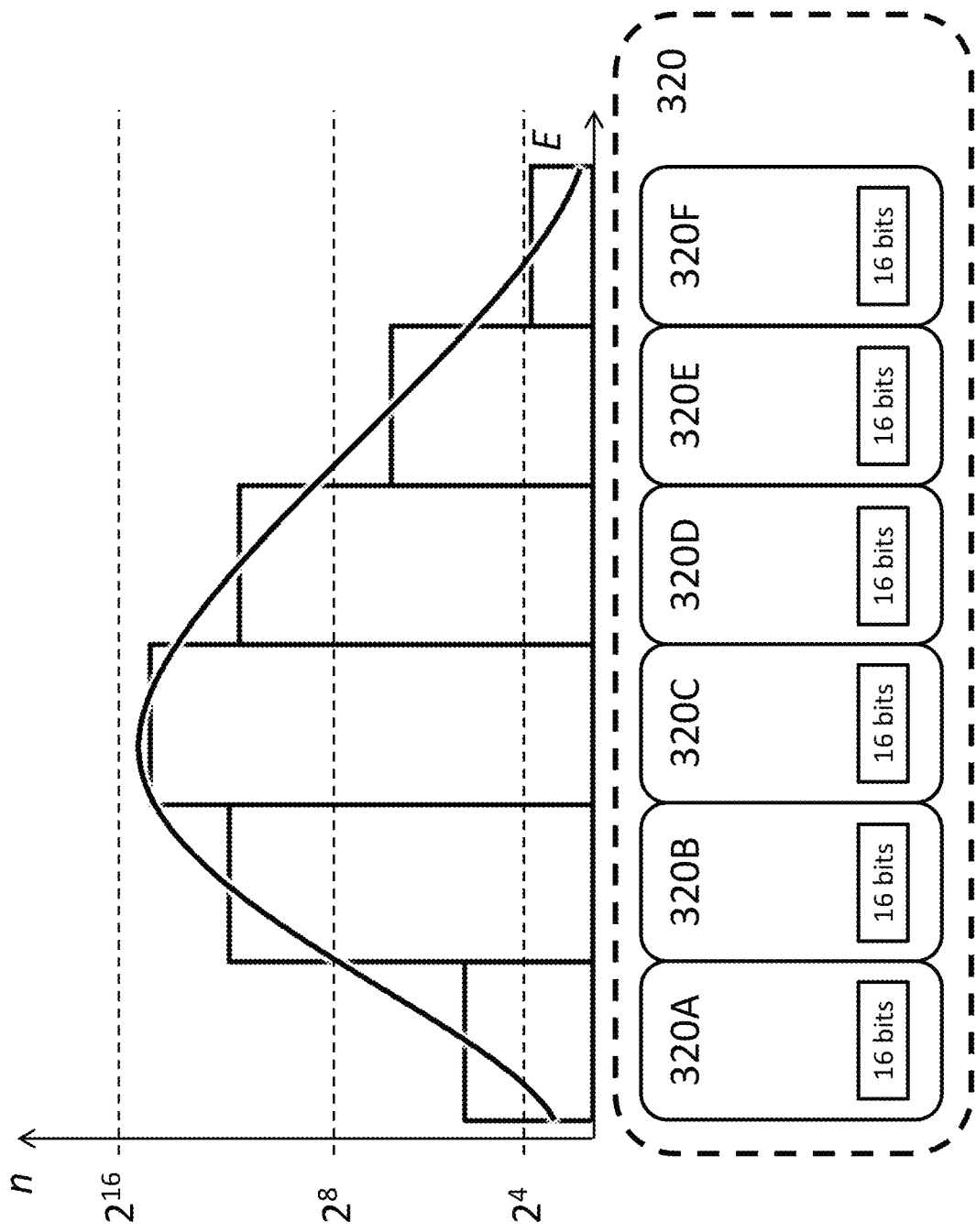
FIG. 4A schematically shows the electronic system with 6 counters, each of which has 16 bits; and the numbers of particles of radiation registered in the counters.
Figure 4B:
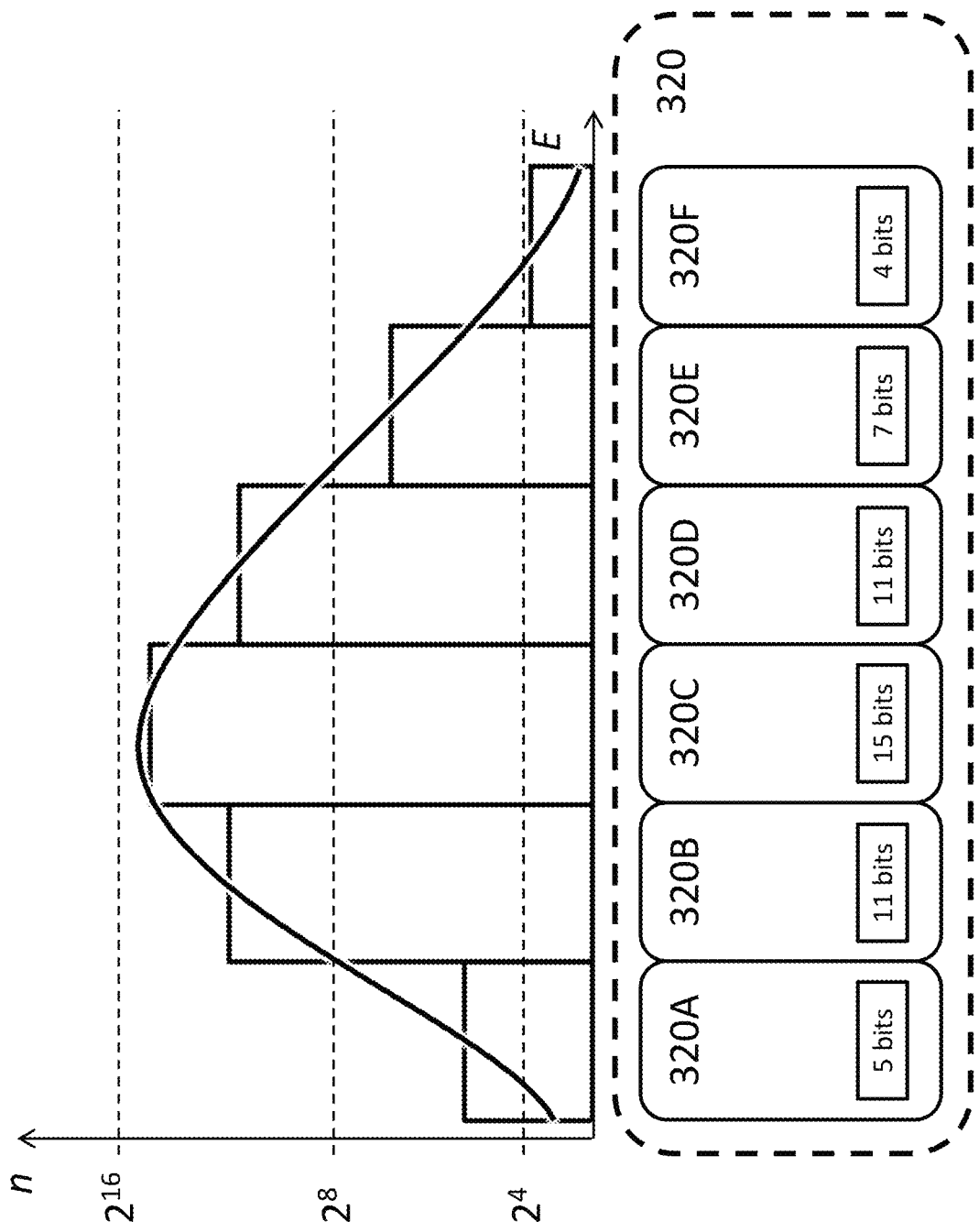
FIG. 4B schematically shows the minimum numbers of bits the counters need to count after a period of time.

In an embodiment, the electronic system 121 includes a plurality of counters 320 (e.g., counters 320A, 320B, 320C, 320D . . . ). The particle counting upper limit of each counter 320 is determined by the number of bits the counter 320 has. For example, a counter comprising 4 bits may count up to 16, and a counter with 16 bits may count up to 65536. A bit may be implemented by any suitable circuit, such as a flip-flop, which is a circuit that has two stable states and can be used to store information, and that can be made to change state by signals applied to one or more control inputs. The numbers of particles of radiation at different energy levels may be quite different due to the nature of the incident radiation. In an example shown in FIG. 4A, the electronic system 121 is configured to count particles at 6 different energy levels by using six counters 320A to 320F, each of which has 16 bits. After a period of time, the numbers of particles of radiation registered in the counters are different—counter 320C has the highest counts of almost $2^{15}$ while counter 320F has the lowest counts of less than 15. Namely, counter 320C need all its 16 bits while counter 320F only need 4 of its 16 bits. FIG. 4B shows the minimum numbers of bits the counters need to register their respective counts in FIG. 4A.

Figure 5A:
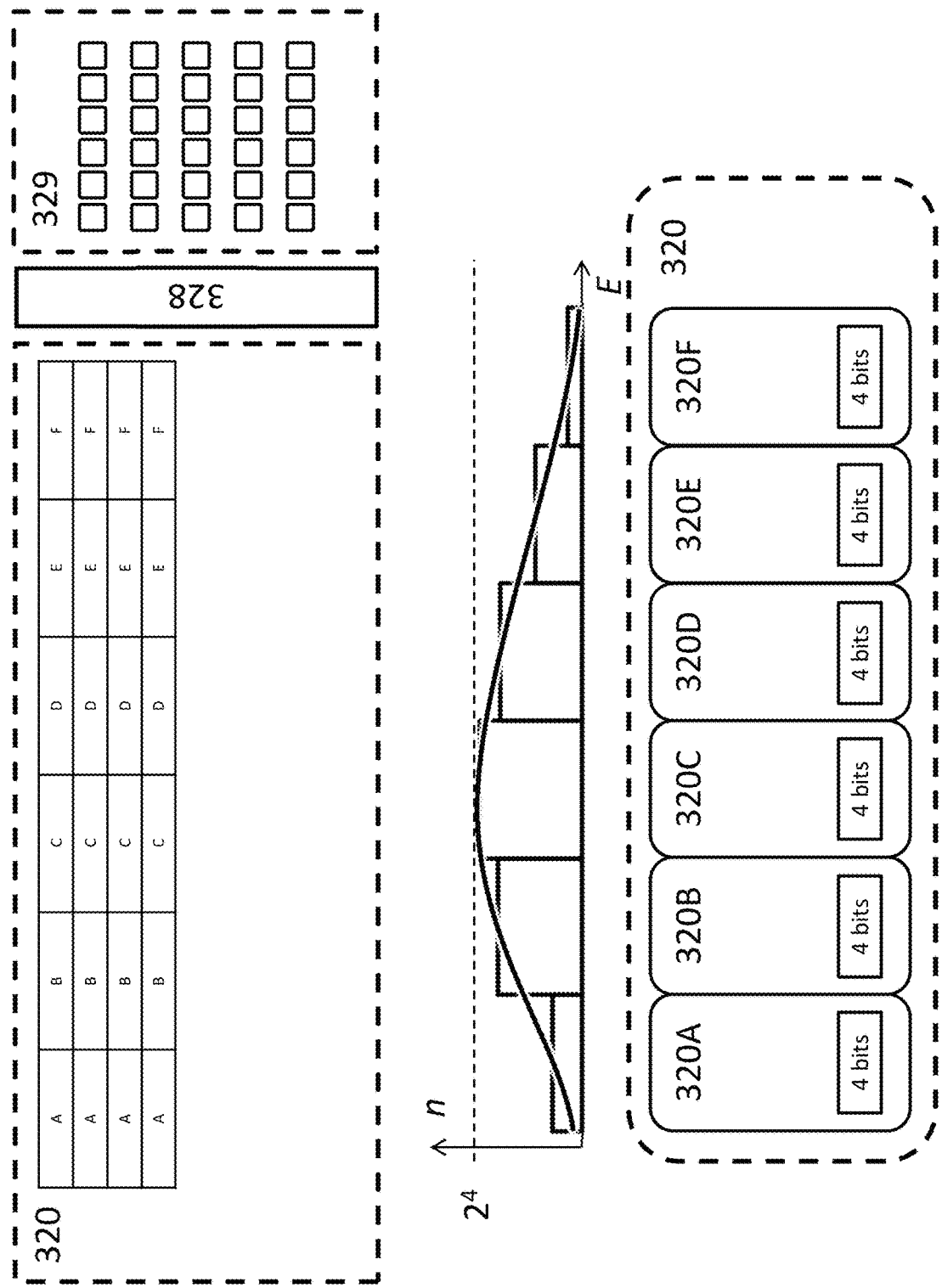
FIG. 5A schematically shows some memory units allocated to the counters before the counting starts.

In an embodiment, the radiation detector 100 may have a memory 329 and a processor 328 configured to dynamically allocate units of the memory to those counters that need more memory during the particle counting. The units may be any number of bits (e.g., one bit). The memory 329 may have at least 100, 2500, 10000, or more units. Each pixel of the radiation detector 100 may have its dedicated memory 329 or the pixels may share the memory 329. In an embodiment, each counter may have some units initially allocated to the counter, before the counting starts. As shown in FIG. 5A, counters 320A to 320F initially all have 4 bits allocated thereto, which allow each counter to count up to 15 particles.

Figure 5B:
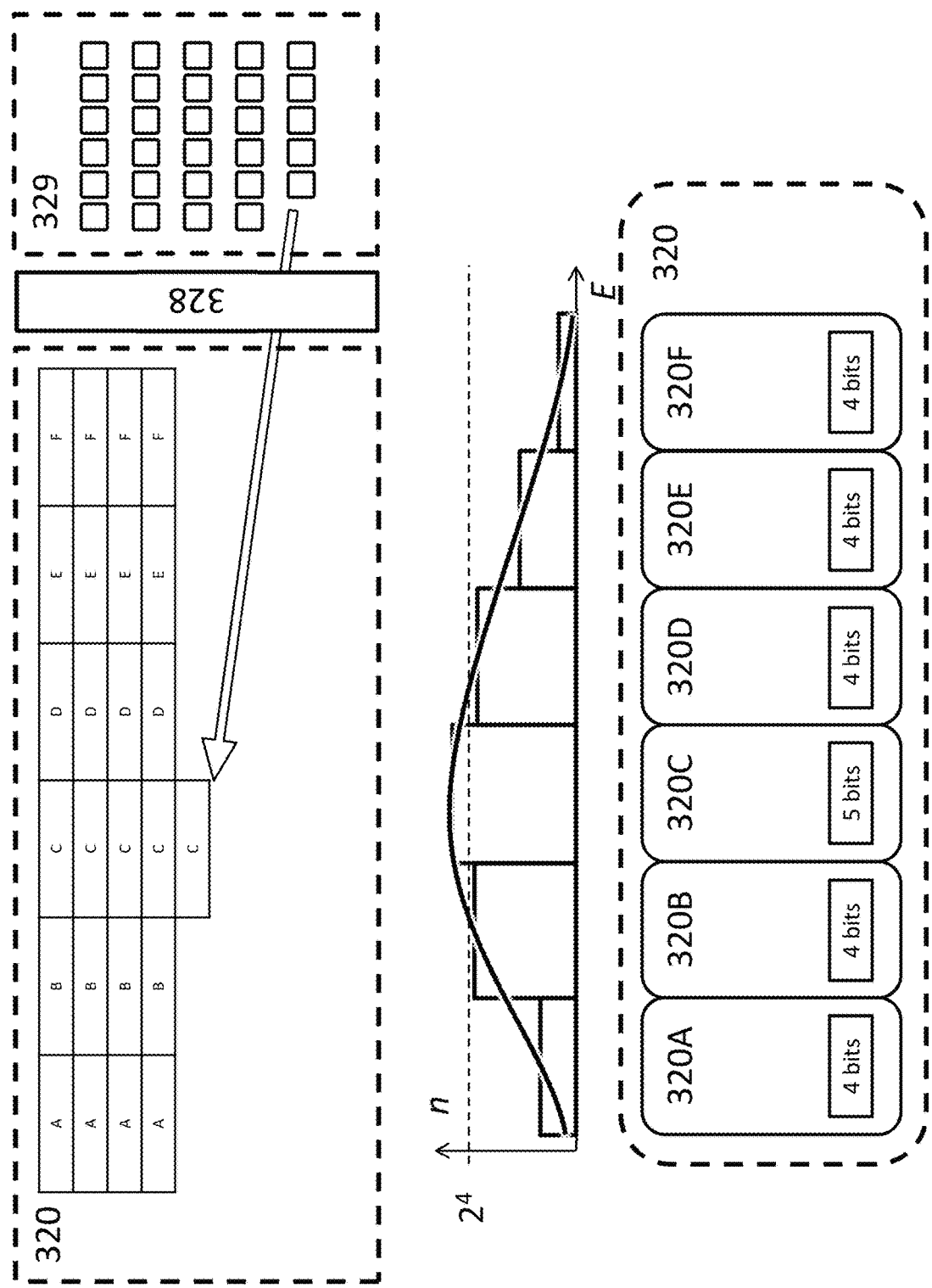
FIG. 5B schematically shows the processor 328 may allocate one additional unit from the memory to one of the counters.

As the counting progresses, the particle numbers registered in the counters may increase, but possibly at different rates. Some of the counters may reach the maximum that their initially allocated units of the memory 329 allow before others of the counter do. In the example shown in FIG. 5B, before counter 320C will reach the maximum of 15 its initially allocated 4 bits allow, the processor 328 may allocate an addition unit (e.g., one bit) from the memory 329 to counter 320C before counter 320C overflows. The maximum of counts of counter 320C thus increases above 16 (e.g., to 32).

Figure 5C:
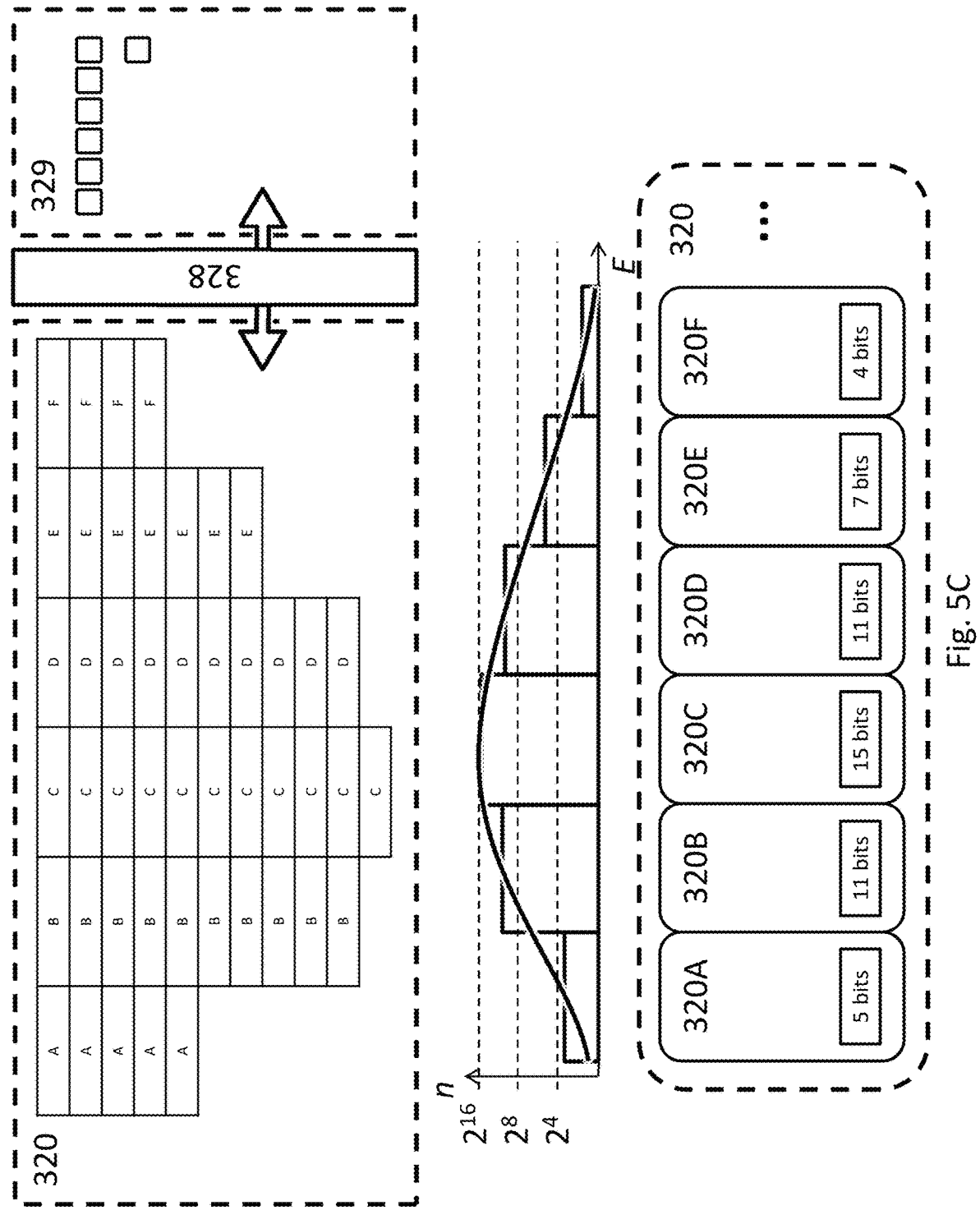
FIG. 5C schematically shows the processor has allocated many memory units to the counters.

The processor 328 is configured to monitor the numbers of radiation particles registered in the counters. If the registered numbers of particles in the counters satisfy a condition (e.g., reaching a threshold value, or the rate of change of the registered numbers reaching a threshold rate), the controller 328 is configured to allocate a unit from the memory 329 to the counters. In the example shown in FIG. 5C, the processor 328 has allocated many units to the counters. For example, counter 320C now has 15 bits, while counter 320F still has the initially allocated 4 bits.

In an embodiment, the processor 328 is configured to deallocate the units from the counters back to the memory 329, if the registered particle numbers of the counters satisfy a condition (e.g., remaining below a threshold value, or the rate of change of the registered numbers remaining below a threshold rate). The deallocated units may be reallocated to the counters as needed.

Figure 6A:
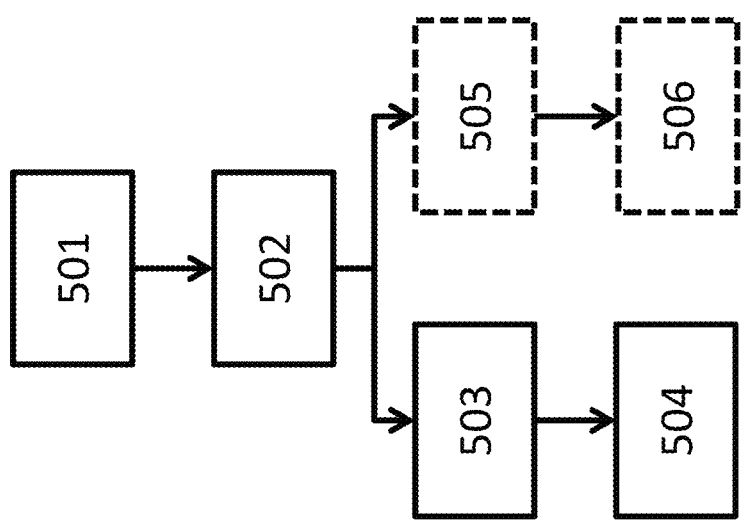
FIG. 6A and FIG. 6B each show a flowchart for a method according to an embodiment.

FIG. 6A schematically shows an example flowchart of a method of dynamic allocation of memory units in a radiation detector. In procedure 501, it is determined whether an energy of a particles of radiation (e.g., one of those absorbed by the radiation absorption layer of the detector) falls into a bin. In procedure 502, if the energy of the particle falls into the bin as determined in procedure 501, the number of particles registered in a counter associated with that bin is increased by one. In procedure 503, it is determined whether the number of particles registered or a rate of change thereof satisfies a condition (e.g., the number or rate equals or exceeds a threshold value or rate). In procedure 504, if the condition is satisfied as determined in procedure 503, a unit of memory is allocated to that counter. In optional procedure 505, it is determined whether a number of particles registered in another counter or the rate of change thereof satisfies another condition (e.g., the number or rate equals or is below a threshold value or rate). In optional procedure 506, if the number of particles registered in the other counter or the rate of change thereof satisfies the other condition, a unit of memory is deallocated from the other counter and returned to the memory.

Figure 6B:
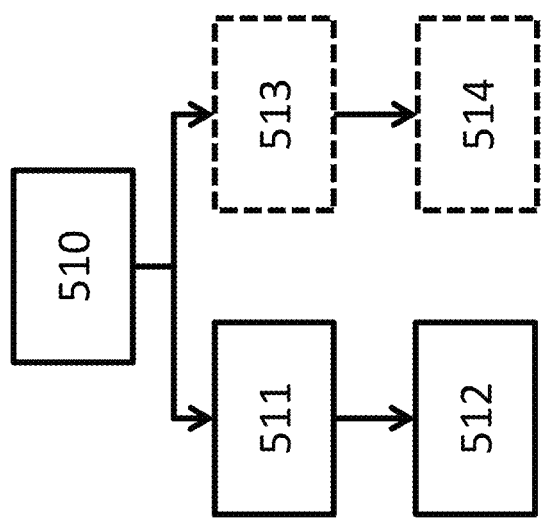

FIG. 6B schematically shows another example of flowchart of a method of dynamic allocation of memory units in a radiation detector. In procedure 510, a number registered by a counter configured to count only particles of radiation whose energy falls into a bin is monitored. In procedure 511, it is determined whether the number or a rate of change thereof satisfies a first condition (e.g., the number or rate equals or exceeds a threshold value or rate). In procedure 512, if the first condition is satisfied as determined in procedure 511, a unit of memory is allocated to that counter. In optional procedure 513, it is determined whether the number or a rate of change thereof satisfies a second condition (e.g., the number or rate equals or is below a threshold value or rate). In optional procedure 514, if the number or the rate of change thereof satisfies the second condition, a unit of memory is deallocated from the counter and returned to the memory.

Figure 7:
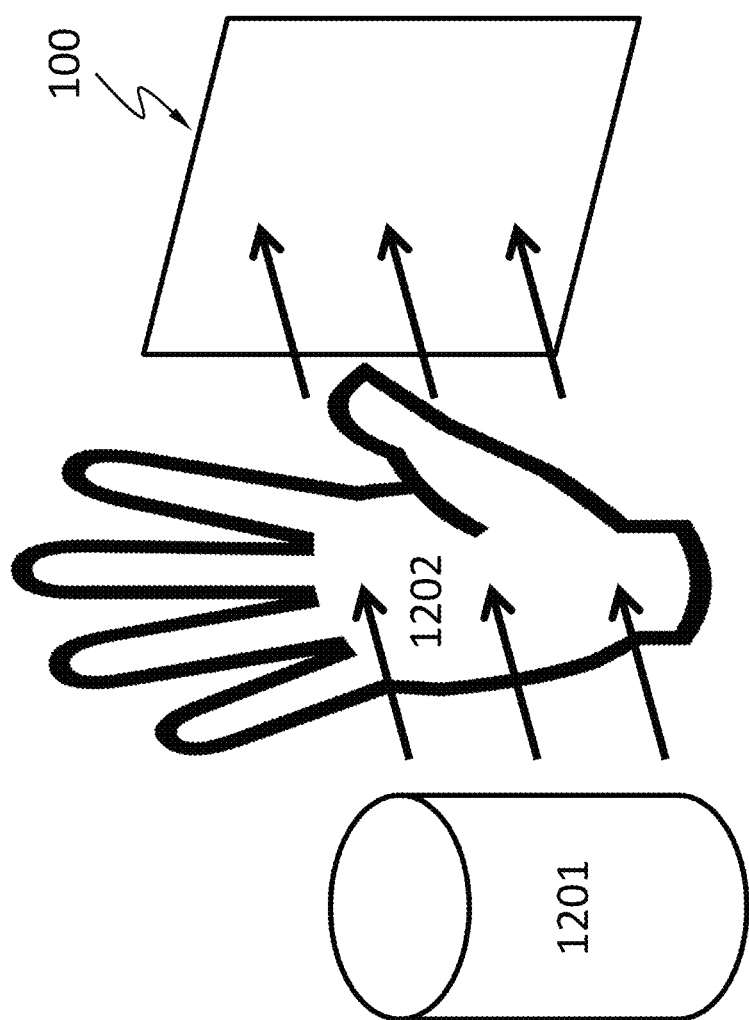
FIG. 7-FIG. 13 each schematically show a system comprising the radiation detector described herein.

FIG. 7 schematically shows a system comprising the radiation detector 100 described herein. The system may be used for medical imaging such as chest X-ray radiography, abdominal X-ray radiography, etc. The system comprises a pulsed radiation source 1201 that emits X-ray. X-ray emitted from the pulsed radiation source 1201 penetrates an object 1202 (e.g., a human body part such as chest, limb, abdomen), is attenuated by different degrees by the internal structures of the object 1202 (e.g., bones, muscle, fat and organs, etc.), and is projected to the radiation detector 100. The radiation detector 100 forms an image by detecting the intensity distribution of the X-ray.

Figure 8:
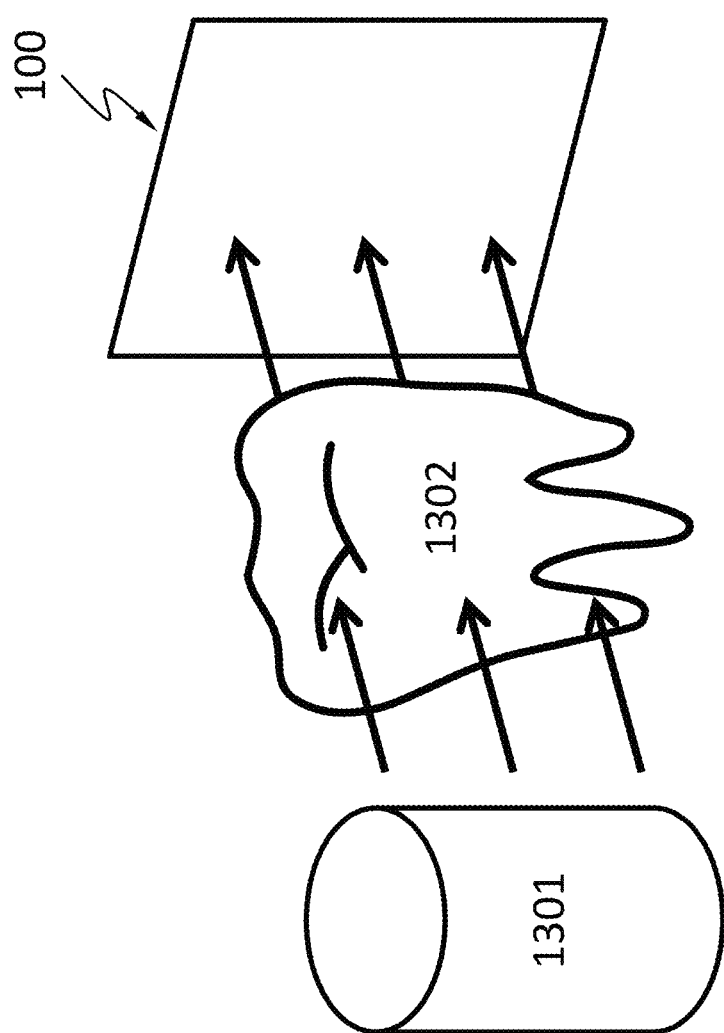

FIG. 8 schematically shows a system comprising the radiation detector 100 described herein. The system may be used for medical imaging such as dental X-ray radiography. The system comprises a pulsed radiation source 1301 that emits X-ray. X-ray emitted from the pulsed radiation source 1301 penetrates an object 1302 that is part of a mammal (e.g., human) mouth. The object 1302 may include a maxilla bone, a palate bone, a tooth, the mandible, or the tongue. The X-ray is attenuated by different degrees by the different structures of the object 1302 and is projected to the radiation detector 100. The radiation detector 100 forms an image by detecting the intensity distribution of the X-ray. Teeth absorb X-ray more than dental caries, infections, periodontal ligament. The dosage of X-ray radiation received by a dental patient is typically small (around 0.150 mSv for a full mouth series).

Figure 9:
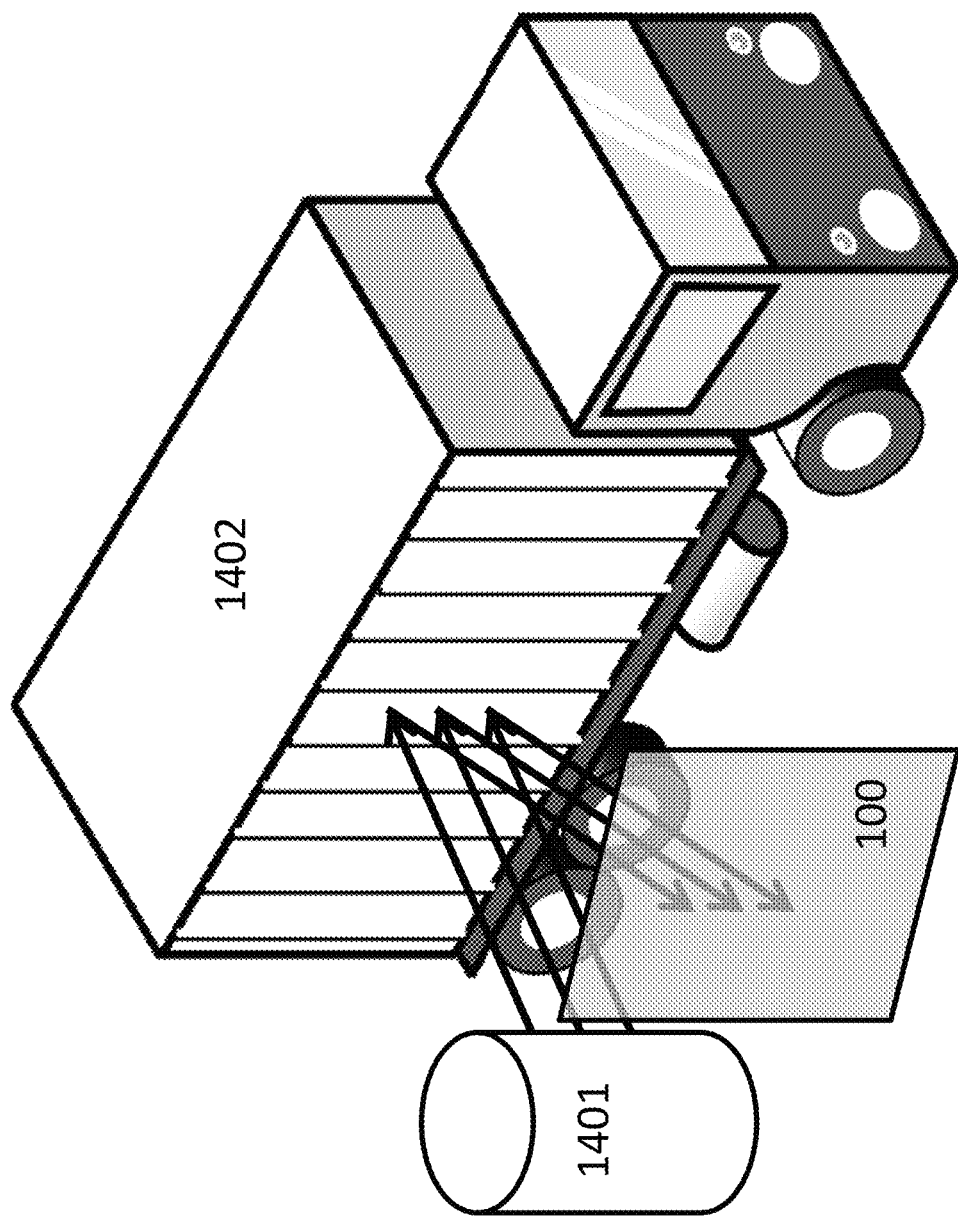

FIG. 9 schematically shows a cargo scanning or non-intrusive inspection (NII) system comprising the radiation detector 100 described herein. The system may be used for inspecting and identifying goods in transportation systems such as shipping containers, vehicles, ships, luggage, etc. The system comprises a pulsed radiation source 1401. Radiation emitted from the pulsed radiation source 1401 may backscatter from an object 1402 (e.g., shipping containers, vehicles, ships, etc.) and be projected to the radiation detector 100. Different internal structures of the object 1402 may backscatter the radiation differently. The radiation detector 100 forms an image by detecting the intensity distribution of the backscattered radiation and/or energies of the backscattered radiation.

Figure 10:
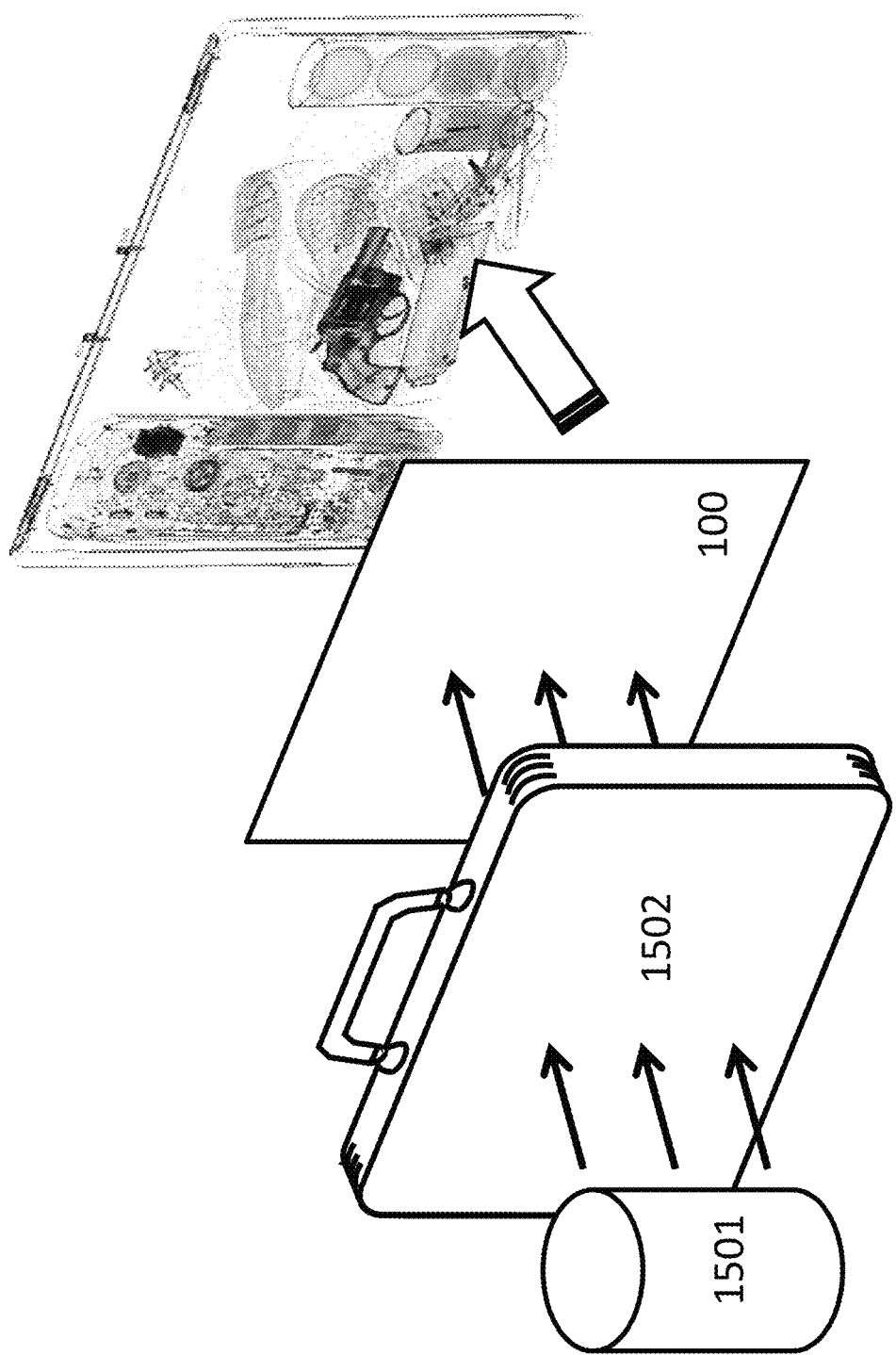

FIG. 10 schematically shows another cargo scanning or non-intrusive inspection (Nil) system comprising the radiation detector 100 described herein. The system may be used for luggage screening at public transportation stations and airports. The system comprises a pulsed radiation source 1501 that emits X-ray. X-ray emitted from the pulsed radiation source 1501 may penetrate a piece of luggage 1502, be differently attenuated by the contents of the luggage, and projected to the radiation detector 100. The radiation detector 100 forms an image by detecting the intensity distribution of the transmitted X-ray. The system may reveal contents of luggage and identify items forbidden on public transportation, such as firearms, narcotics, edged weapons, flammables.

Figure 11:
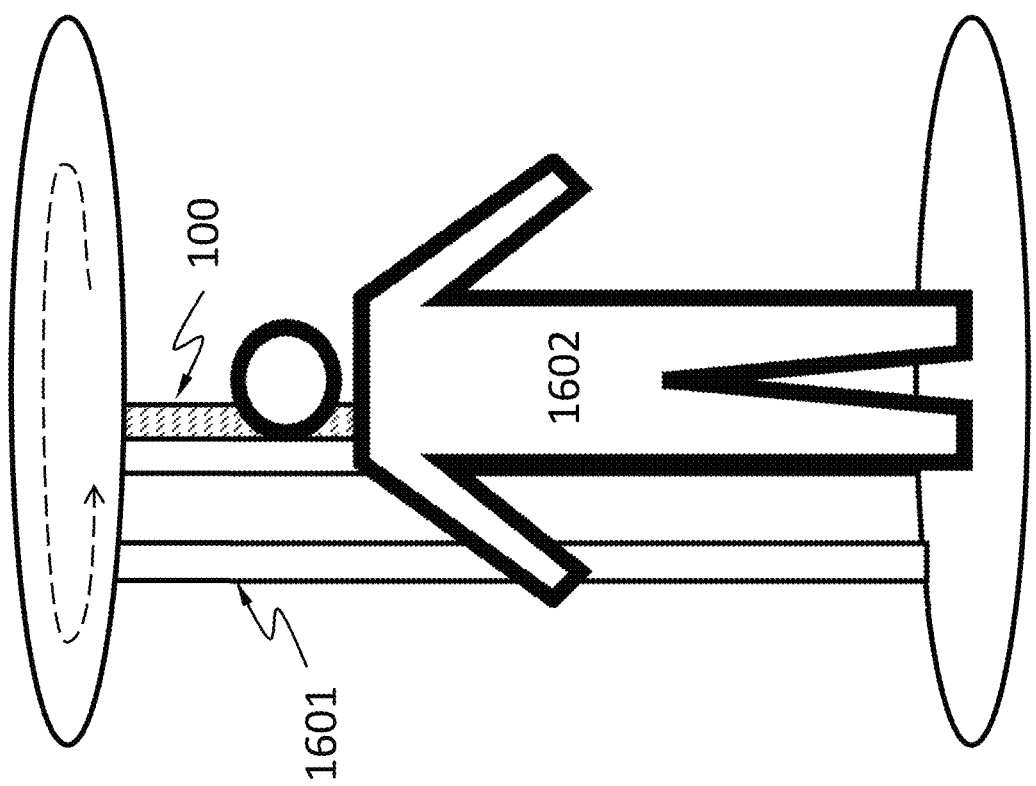

FIG. 11 schematically shows a full-body scanner system comprising the radiation detector 100 described herein. The full-body scanner system may detect objects on a person's body for security screening purposes, without physically removing clothes or making physical contact. The full-body scanner system may be able to detect non-metal objects. The full-body scanner system comprises a pulsed radiation source 1601. The radiation emitted from the pulsed radiation source 1601 may backscatter from a human 1602 being screened and objects thereon, and be projected to the radiation detector 100. The objects and the human body may backscatter the radiation differently. The radiation detector 100 forms an image by detecting the intensity distribution of the backscattered radiation. The radiation detector 100 and the pulsed radiation source 1601 may be configured to scan the human in a linear or rotational direction.

Figure 12:
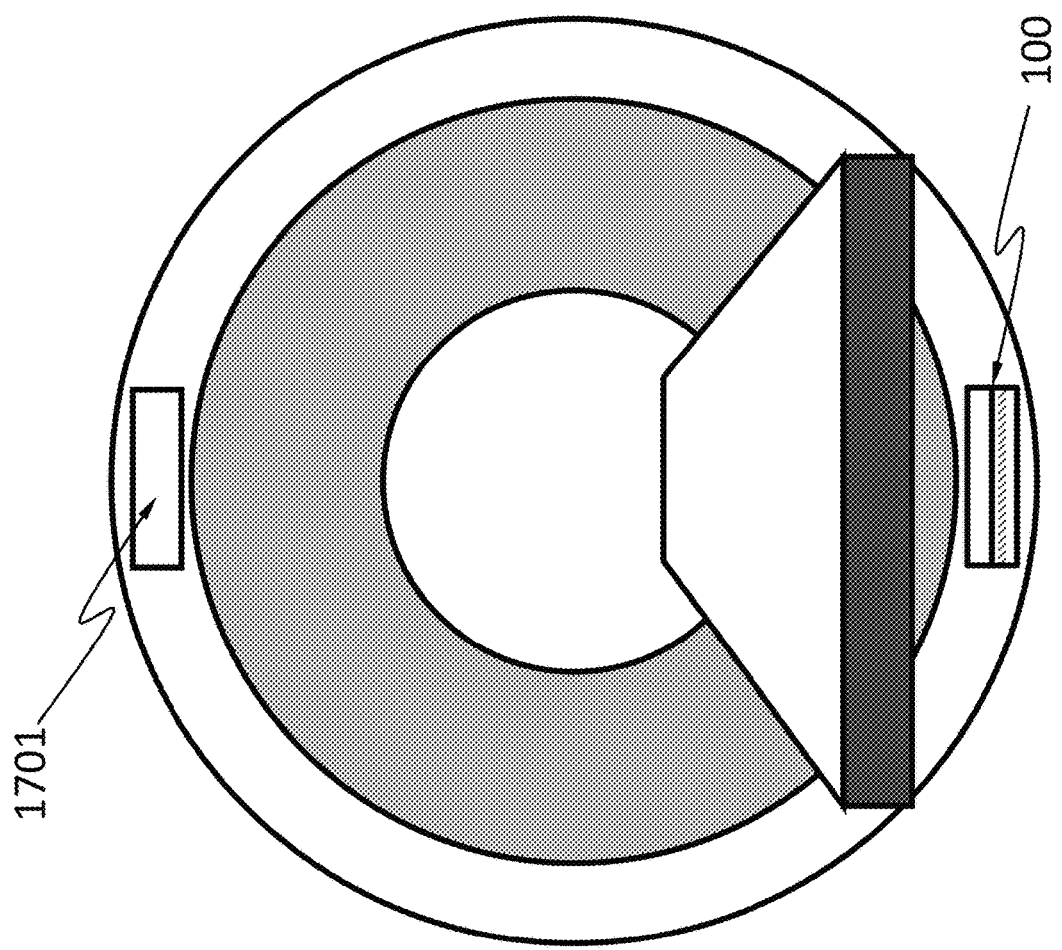

FIG. 12 schematically shows an X-ray computed tomography (X-ray CT) system. The X-ray CT system uses computer-processed X-rays to produce tomographic images (virtual "slices") of specific areas of a scanned object. The tomographic images may be used for diagnostic and therapeutic purposes in various medical disciplines, or for flaw detection, failure analysis, metrology, assembly analysis and reverse engineering. The X-ray CT system comprises the radiation detector 100 described herein and a pulsed radiation source 1701 that emits X-ray. The radiation detector 100 and the pulsed radiation source 1701 may be configured to rotate synchronously along one or more circular or spiral paths.

Figure 13:
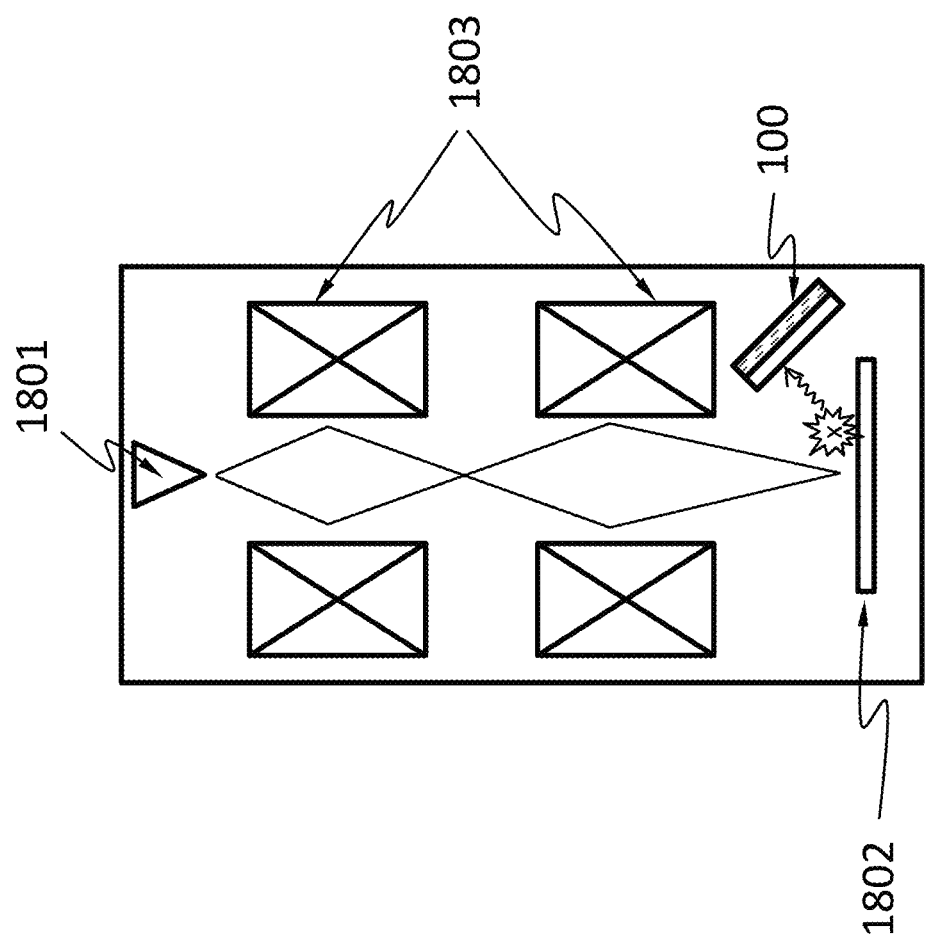

FIG. 13 schematically shows an electron microscope. The electron microscope comprises an electron source 1801 (also called an electron gun) that is configured to emit electrons. The electron source 1801 may have various emission mechanisms such as thermionic, photocathode, cold emission, or plasmas source. The emitted electrons pass through an electronic optical system 1803, which may be configured to shape, accelerate, or focus the electrons. The electrons then reach a sample 1802 and an image detector may form an image therefrom. The electron microscope may comprise the radiation detector 100 described herein, for performing energy-dispersive X-ray spectroscopy (EDS). EDS is an analytical technique used for the elemental analysis or chemical characterization of a sample. When the electrons incident on a sample, they cause emission of characteristic X-rays from the sample. The incident electrons may excite an electron in an inner shell of an atom in the sample, ejecting it from the shell while creating an electron hole where the electron was. An electron from an outer, higher-energy shell then fills the hole, and the difference in energy between the higher-energy shell and the lower energy shell may be released in the form of an X-ray. The number and energy of the X-rays emitted from the sample can be measured by the radiation detector 100.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A radiation detector, comprising:
   a radiation absorption layer configured to absorb a radiation;
   a plurality of counters each configured to register a count of particles of the radiation that are absorbed by the radiation absorption layer and have energy in an interval associated therewith;
   a memory comprising units;
   a processor configured to allocate the units to the plurality of counters;
   wherein the processor is configured to allocate the units to the plurality of counters based on at least one count of particles registered in at least one of the plurality of counters or a rate of change of at least one count of particles registered in at least one of the plurality of counters.

2. The radiation detector of claim 1, wherein the processor is configured to deallocate the units.

3. The radiation detector of claim 2, wherein the processor is configured to deallocate the units to the plurality of counters based on at least one count of particles registered in at least one of the plurality of counters.

4. The radiation detector of claim 2, wherein the processor is configured to deallocate the units to the plurality of counters based on a rate of change of at least one count of particles registered in at least one of the plurality of counters.

5. The radiation detector of claim 1, wherein the radiation is X-ray.

6. The radiation detector of claim 1, further comprising:
a controller;
wherein the controller is configured to determine whether an energy of a particle of the radiation is in the interval associated with a first counter among the plurality of counters;
wherein the controller is configured to cause the count registered by the first counter to increase by one.

7. The radiation detector of claim 6, further comprising:
a first voltage comparator configured to compare a voltage of an electric contact of the radiation absorption layer to a first threshold;
a second voltage comparator configured to compare the voltage to a second threshold;
wherein the controller is configured to start a time delay from a time at which the first voltage comparator determines that an absolute value of the voltage equals or exceeds an absolute value of the first threshold.

8. The radiation detector of claim 7, wherein the controller is configured to activate the second voltage comparator at a beginning or expiration of the time delay.

9. The radiation detector of claim 7, further comprising a voltmeter, wherein the controller is configured to cause the voltmeter to measure the voltage upon expiration of the time delay.

10. The radiation detector of claim 9, wherein the controller is configured to determine the energy based on a value of the voltage measured upon expiration of the time delay.

11. The radiation detector of claim 7, further comprising a capacitor module electrically connected to the electric contact, wherein the capacitor module is configured to collect charge carriers from the electric contact.

12. The radiation detector of claim 7, wherein the controller is configured to connect the electric contact to an electrical ground.

13. The radiation detector of claim 7, wherein a rate of change of the voltage is substantially zero at expiration of the time delay.

14. The radiation detector of claim 1, wherein the radiation absorption layer comprises a diode.

15. The radiation detector of claim 1, wherein the radiation absorption layer comprises silicon, germanium, GaAs, CdTe, CdZnTe, or a combination thereof.

16. The radiation detector of claim 1, wherein the radiation detector does not comprise a scintillator.

17. A system comprising the radiation detector of claim 1 and a radiation source.

18. A method comprising:
determining whether energy of a particle of a radiation is in an interval;
upon determination that the energy is in the interval, causing a first count registered by a first counter associated with the interval to increase by one;
determining whether the first count or a rate of change thereof satisfies a first condition;
upon determination that the first count or the rate of change thereof satisfies the first condition, allocating a unit of a memory to the first counter.

19. The method of claim 18, further comprising:
determining whether a second count registered by a second counter or a rate of change thereof satisfies a second condition;
upon determination that the second count or the rate of change thereof satisfies the second condition, deallocating a unit of a memory from the second counter.

20. A method comprising:
monitoring a count registered by a counter configured to count only particles of a radiation, energy of each of the particles being within an interval;
determining whether the count or a rate of change thereof satisfies a first condition;
upon determination that the count or the rate of change thereof satisfies the first condition, allocating a unit of a memory to the counter.

21. The method of claim 20, further comprising:
determining whether the count or the rate of change thereof satisfies a second condition;
upon determination that the count or the rate of change thereof satisfies the second condition, deallocating a unit of the memory from the counter.

22. A radiation detector, comprising:
a radiation absorption layer configured to absorb a radiation;
a plurality of counters each configured to register a count of particles of the radiation that are absorbed by the radiation absorption layer and have energy in an interval associated therewith;
a memory comprising units;
a processor configured to allocate the units to the plurality of counters and deallocate the units;
wherein the processor is configured to deallocate the units to the plurality of counters based on at least one count of particles registered in at least one of the plurality of counters or a rate of change of at least one count of particles registered in at least one of the plurality of counters.

23. The radiation detector of claim 22, wherein the radiation is X-ray.

24. The radiation detector of claim 22, further comprising:
a controller;
wherein the controller is configured to determine whether an energy of a particle of the radiation is in the interval associated with a first counter among the plurality of counters;
wherein the controller is configured to cause the count registered by the first counter to increase by one.

25. The radiation detector of claim 24, further comprising:
a first voltage comparator configured to compare a voltage of an electric contact of the radiation absorption layer to a first threshold;
a second voltage comparator configured to compare the voltage to a second threshold;
wherein the controller is configured to start a time delay from a time at which the first voltage comparator determines that an absolute value of the voltage equals or exceeds an absolute value of the first threshold.

26. The radiation detector of claim 25, wherein the controller is configured to activate the second voltage comparator at a beginning or expiration of the time delay.

27. The radiation detector of claim 25, further comprising a voltmeter, wherein the controller is configured to cause the voltmeter to measure the voltage upon expiration of the time delay.

28. The radiation detector of claim 27, wherein the controller is configured to determine the energy based on a value of the voltage measured upon expiration of the time delay.

29. The radiation detector of claim 25, further comprising a capacitor module electrically connected to the electric contact, wherein the capacitor module is configured to collect charge carriers from the electric contact.

30. The radiation detector of claim 25, wherein the controller is configured to connect the electric contact to an electrical ground.

31. The radiation detector of claim 25, wherein a rate of change of the voltage is substantially zero at expiration of the time delay.

32. The radiation detector of claim 22, wherein the radiation absorption layer comprises a diode.

33. The radiation detector of claim 22, wherein the radiation absorption layer comprises silicon, germanium, GaAs, CdTe, CdZnTe, or a combination thereof.

34. The radiation detector of claim 22, wherein the radiation detector does not comprise a scintillator.

35. A system comprising the radiation detector of claim 22 and a radiation source.

* * * * *